United States Patent
Badoz

(10) Patent No.: US 7,249,414 B2
(45) Date of Patent: Jul. 31, 2007

(54) METHOD FOR MAKING A ROOT CANAL INSTRUMENT

(75) Inventor: Jean-Marie Badoz, Doubs (FR)

(73) Assignee: Micro Mega, S.A., Besançon (FR)

( * ) Notice: Subject to any disclaimer, the term of this patent is extended or adjusted under 35 U.S.C. 154(b) by 479 days.

(21) Appl. No.: 10/813,381

(22) Filed: Mar. 30, 2004

(65) Prior Publication Data
US 2004/0185414 A1    Sep. 23, 2004

Related U.S. Application Data

(63) Continuation-in-part of application No. 10/049,349, filed on Jan. 30, 2002, now abandoned.

(30) Foreign Application Priority Data
Sep. 10, 1999   (FR) .................................. 99 11448

(51) Int. Cl.
A61C 5/02    (2006.01)
B23P 13/00   (2006.01)

(52) U.S. Cl. .................. 29/896.1; 29/896.11; 29/557; 29/558; 433/102

(58) Field of Classification Search ............. 29/896.1, 29/896.11, 557, 558; 433/102
See application file for complete search history.

(56) References Cited

U.S. PATENT DOCUMENTS

| | | | |
|---|---|---|---|
| 4,604,884 A | 8/1986 | Matsutani | |
| 5,464,362 A | 11/1995 | Heath et al. | |
| 5,752,825 A | 5/1998 | Buchanan | |
| 5,857,852 A | 1/1999 | Garman | |
| 5,873,719 A * | 2/1999 | Calas et al. | 433/102 |
| 5,882,198 A | 3/1999 | Taylor et al. | |
| 5,938,440 A | 8/1999 | McSpadden | |
| 5,975,899 A * | 11/1999 | Badoz et al. | 433/102 |
| 5,984,679 A | 11/1999 | Farzin-Nia et al. | |
| 6,299,445 B1 | 10/2001 | Garman | |

FOREIGN PATENT DOCUMENTS

| | | |
|---|---|---|
| CH | 670756 | 7/1989 |
| FR | 9604987 | 10/1997 |
| FR | 9614347 | 5/1998 |
| WO | WO 97 21392 | 6/1997 |
| WO | WO 99 37235 | 7/1999 |
| WO | WO 99 43469 | 9/1999 |

* cited by examiner

*Primary Examiner*—Essama Omgba
(74) *Attorney, Agent, or Firm*—Gary M. Cohen

(57) ABSTRACT

Alternative methods are described for machining a root-canal instrument, such as a root-canal reamer, which includes a working section having three flutes forming three cutting lips which are located at the apices of an isosceles triangle.

13 Claims, 2 Drawing Sheets

METHOD FOR MAKING A ROOT CANAL INSTRUMENT

RELATED CASE

This is a continuation-in-part of U.S. patent application Ser. No. 10/049,349, filed Jan. 30, 2002, which has since been abandoned.

BACKGROUND OF THE INVENTION

The present invention relates to the production of endodontic instruments for preparing dental canals, and more particularly, to a type of canal instrument which is known as a "dental reamer" and which has a working cross-section, called a "blade", which comprises three flutes forming three cutting lips.

Canal instruments which have a working cross-section comprised of three flutes forming three cutting lips are known in the art. In particular, this type of instrument is known from prior French Patent Applications No. 96 04987 and No. 96 14347.

The instruments described in these Patent Applications have a circular symmetry, on the order of three or more, depending on the number of cutting lips of the instrument. As a result, when the instrument is used (rotated) in a curved dental canal, the instrument follows the axis of the canal by virtue of the equilibrium of the forces applied to the instrument.

This type of instrument is satisfactory, except when the canal cannot be assimilated to a hole having a circular cross-section. This is because, in this latter case, the forces applied during preparation of the canal are no longer in equilibrium, and there is a risk that the trajectory of the instrument will deviate from the axis of the dental canal. This deviation can have very serious consequences since it can lead to the formation of an incorrect path, or even a perforation of the canal.

SUMMARY OF THE INVENTION

It is the object of the present invention to remedy the disadvantages of prior dental reamers of this general type by providing an instrument having a blade which makes it possible to eliminate such risks.

This is achieved by deliberately breaking the circular symmetry of the instrument in such a way that, as the resistance of the blade to bending is no longer the same in all directions, the point of the instrument is made to seek out the dental canal and to naturally penetrate into the dental canal. To this end, the canal instrument of the present invention is produced by a grinding method which provides the canal instrument with a working cross-section comprised of three flutes, forming three cutting lips, wherein the three cutting lips are situated at the vertices of an isosceles triangle, rather than an equilateral triangle.

The present invention will be better understood from the following description of illustrative embodiments, which are given as non-limiting examples, with reference to the following drawings.

DETAILED DESCRIPTION OF THE INVENTION

The present invention is generally directed to a type of canal instrument which is generally known as a "dental reamer". Such canal instruments generally include a working cross-section 10 which comprises three flutes 20, 21, 22 forming three cutting lips 30, 31, 32. The three flutes 20, 21, 22 have an "S" shape. The three cutting lips 30, 31, 32 are situated at the vertices of a triangle.

Like all canal instruments of this type, the instrument produced in accordance with the present invention has a working cross-section 10, also referred to as the "blade", having an active part. The working cross-section 10 is obtained by a grinding process and has a conical shape (also obtained by a grinding process). The conical shape is obtained, in most cases, by progressively moving a grinding wheel away from the axis of the instrument as one proceeds away from the point (i.e., the tip) of the instrument.

Figure 1:
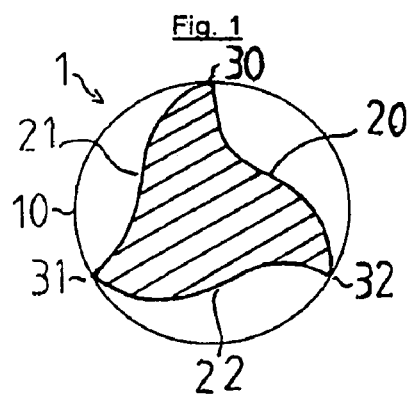
FIG. 1 illustrates a cross-sectional view of a prior canal instrument, having three cutting lips which are situated at the vertices of an equilateral triangle.

FIG. 1 shows a prior canal instrument 1, which is obtained by machining three identical flutes 20, 21, 22 forming three cutting lips 30, 31, 32 arranged at 120° and situated at the vertices of an equilateral triangle.

Figure 2:
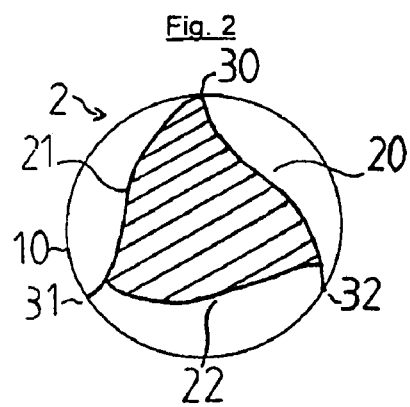
FIG. 2 illustrates a cross-sectional view of a canal instrument produced in accordance with the present invention, which is obtained by a first alternative method of production.
Figure 3:
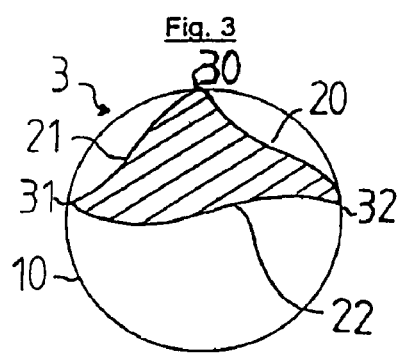
FIG. 3 illustrates a cross-sectional view of a canal instrument produced in accordance with the present invention, which is obtained by a second alternative method of production.
Figure 4:
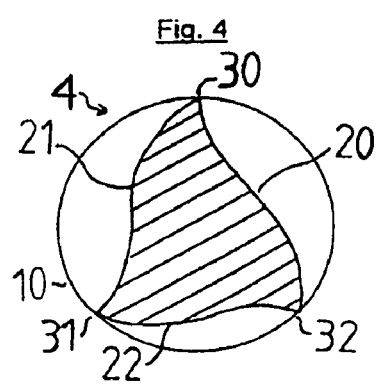
FIG. 4 illustrates a cross-sectional view of a canal instrument produced in accordance with the present invention, which is obtained by a third alternative method of production.

FIGS. 2 to 4 show different methods for producing a canal instrument 2, 3, 4 which is obtained by machining the flutes 20, 21, 22 to form three cutting lips 30, 31, 32 which are situated at the vertices of an isosceles triangle, in accordance with the present invention.

FIG. 2 illustrates a first possible method for producing an instrument 2 in accordance with the present invention. In this method, two flutes 20, 21 are produced by performing two identical, successive machining operations at 120°. A third flute 22 is then produced by performing a third machining operation at a greater depth than the first two machining operations.

It is also possible to make the depth of the third flute 22 greater than the depth of the first two flutes 20, 21 at the point of the working cross-section 10 of the instrument, which then becomes identical to the depth of the first two flutes 20, 21. The depth of the third flute 22 can become identical to the depth of the first two flutes 20, 21 either at the end of the working cross-section 10 or before the end of the working cross-section 10.

FIG. 3 illustrates a second possible method for producing an instrument 3 in accordance with the present invention. In this method, two flutes 20, 21 are produced by performing two identical, successive machining operations at an angle greater than 120°. The third flute 22 is then produced by performing a third machining operation which complements the first two machining operations.

FIG. 4 illustrates a third possible method for producing an instrument 4 in accordance with the present invention. In this method, two flutes 20, 21 are produced by performing two identical, successive machining operations at an angle less than 120°. The third flute 22 is then produced by performing a third machining operation which complements the first two machining operations.

Each of the previously described machining operations are implemented to create a tap on a cylindrical wire using a grinding wheel. To this end, the wire is passed in front of a rotating grinding wheel while the wire is also driven in rotation. To create as many taps as are needed to produce the desired instrument, the same operations are repeated as many times as are needed to produce the number of taps to be associated with the instrument being produced.

Figure 5:
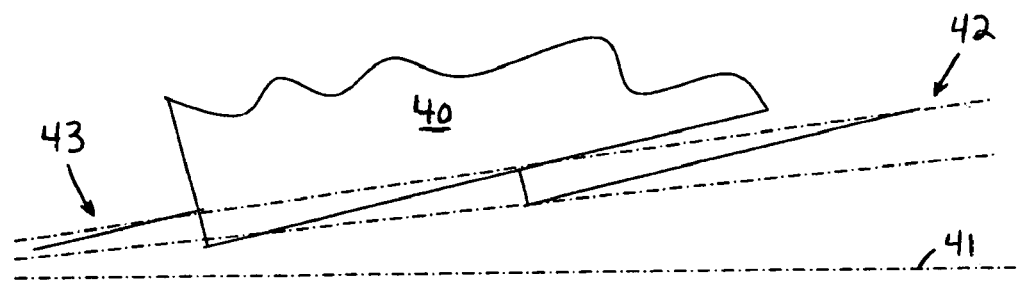
FIG. 5 is a schematic, side elevational view showing the interface between the grinding wheel and a blank which is being machined.

It is generally desirable that the taps have the form of an inverted thread. To this end, and referring to FIG. 5, the grinding wheel 40 must be inclined relative to the axis 41 of the wire 42, and not perpendicular to the axis 41 of the wire 42. While the wire will initially have a generally cylindrical shape, it is further desired that the manufacturing process produce a so-called "working part" 43 having a generally conical shape. This is accomplished by varying the pitch of the spiral which is being produced, so that the pitch increases with increased distance from the point of the instrument, combined with a withdrawal of the grinding wheel during the machining process.

Because the wire used to produce the instrument is flexible, the wire must be guided close to the grinding wheel. This generally requires the use of a jig bushing. For embodiments in which one of the taps is more (or less) deep than the other taps, an offset is created from the departure point for the machining process by advancing (or withdrawing) the grinding wheel relative to the wire.

Figure 6:
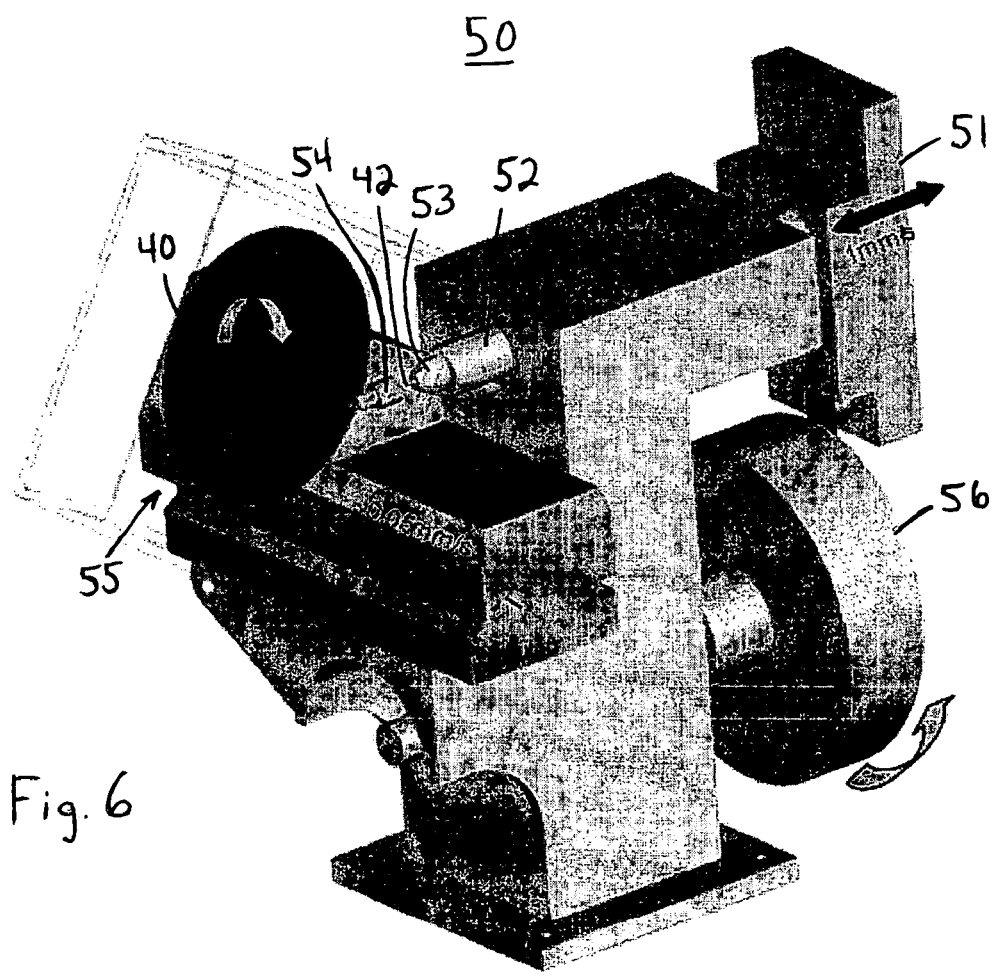
FIG. 6 is an isometric view of an apparatus for performing grinding operations in accordance with the present invention.

A machine 50, and a method for operating the machine to perform the previously described machining operations and produce an instrument 2, 3, 4 in accordance with the present invention, will now be described with reference to FIG. 6.

Blanks of a constant length are first cut out, and then washed. The blanks are then placed in a container (not shown) located at the level of the rearward, mobile part 51. A blank is sent from the mobile part 51 to a clamp 52 through a rotating shaft 53. It should be noted that the mobile part 51, the clamp 52 and the rotating shaft 53 are interlocked longitudinally. The blank is grasped in the clamp 52, and is engaged in a jig bushing 54. The grinding wheel 40 then comes into contact with the wire 42, as a result of the movement of a table 55, at a position between the clamp 52 and the jig bushing 54.

A cam 56 drives the assembly including the mobile part 51, the clamp 52 and the rotating shaft 53 in a forward movement while the clamp 52 and the rotating shaft 53 are in rotation. As the assembly including the mobile part 51, the clamp 52 and the rotating shaft 53 are driven forward, the grinding wheel 40 becomes more distant from the axis 41 of the wire 42. The rate of advance of the assembly including the mobile part 51, the clamp 52 and the rotating shaft 53 will be the same as the rate at which the grinding wheel 40 becomes more distant from the axis 41 of the wire 42. The synchronization of such movement is provided, for example, using geared devices.

When the tap is first created, the grinding wheel 40 will be separated from the wire 42 by a distance corresponding to the radius of the wire. The cam 56 ensures appropriate withdrawal of the assembly including the mobile part 51, the clamp 52 and the rotating shaft 53 such that the wire 42 will be in the same axial position as it was at the beginning of the operation. To create n taps, the shaft 53 will rotate at an angle of 360°/n, and so on.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. A method for manufacturing a canal instrument having a working cross-section comprising three flutes forming three cutting lips, wherein the three flutes have an "S" shape, and wherein the three cutting lips are located on the working cross-section at positions corresponding to vertices of an isosceles triangle, wherein the canal instrument has a working part with a substantially conical shape which tapers to a tip, wherein the flutes define a spiral having a pitch, and wherein the method comprises the steps of:

grinding first and second flutes in a generally cylindrical blank during first and second machining operations, wherein the first and second machining operations are identical and successive machining operations performed at locations on the blank which are separated by an angle of 120°, and thereafter grinding a third flute in the cylindrical blank by performing a third machining operation, wherein the first and second machining operations are performed at a first depth, and wherein the third machining operation is performed at a second depth which is greater than the first depth; and varying the pitch of the spiral during the first, second and third machining operations so that the pitch increases with increased distance from the tip off the canal instrument.

2. The method of claim 1 wherein the third machining operation is initially performed at the second depth, at the working cross-section of the canal instrument, and is thereafter performed at a depth which becomes identical to the first depth, toward an end of the working cross-section.

3. The method of claim 1 which further includes the step of rotating the blank during the grinding.

4. The method of claim 1 wherein the grinding is performed with a grinding wheel, wherein the blank defines a longitudinal axis, and which further includes the step of inclining the grinding wheel relative to the longitudinal axis of the blank.

5. The method of claim 1 wherein the grinding is performed with a grinding wheel, wherein the blank defines a longitudinal axis, and which further includes the step of withdrawing the grinding wheel relative to the longitudinal axis of the blank.

6. A method for manufacturing a canal instrument having a working cross-section comprising three flutes forming three cutting lips, wherein the three flutes have an "S" shape, and wherein the three cutting lips are located on the working cross-section at positions corresponding to vertices of an isosceles triangle, wherein the canal instrument has a working part with a substantially conical shape which tapers to a tip, wherein the flutes define a spiral having a pitch, and wherein the method comprises the steps of:

grinding first and second flutes in a generally cylindrical blank during first and second machining operations, wherein the first and second machining operations are identical and successive machining operations performed at locations on the blank which are separated by an angle greater than 120°, and thereafter grinding a third flute in the cylindrical blank by performing a third machining operation which complements the first and second machining operations to locate the three cutting lips on the working cross-section at the positions which correspond to the vertices of the isosceles triangle; and varying the pitch of the spiral during the first, second and third machining operations so that the pitch increases with increased distance from the tip of the canal instrument.

7. The method of claim 6 which further includes the step of rotating the blank during the grinding.

8. The method of claim 6 wherein the grinding is performed with a grinding wheel, wherein the blank defines a longitudinal axis, and which further includes the step of inclining the grinding wheel relative to the longitudinal axis of the blank.

9. The method of claim 6 wherein the grinding is performed with a grinding wheel, wherein the blank defines a longitudinal axis, and which further includes the step of withdrawing the grinding wheel relative to the longitudinal axis of the blank.

10. A method for manufacturing a canal instrument having a working cross-section comprising three flutes forming three cutting lips, wherein the three flutes have an "S" shape, and, wherein the three cutting lips are located on the working cross-section at positions corresponding to vertices of an isosceles triangle, wherein the canal instrument has a working part with a substantially conical shape which tapers to a tip, wherein the flutes define a spiral having a pitch, and wherein the method comprises the steps of:

grinding first and second flutes in a generally cylindrical blank during first and second machining operations, wherein the first and second machining operations are identical and successive machining operations performed at locations on the blank which are separated by an angle less than 120°, and thereafter grinding a third flute in the cylindrical blank by performing a third machining operation which complements the first and second machining operations to locate the three cutting lips on the working cross-section at the positions which correspond to the vertices of the isosceles triangle; and varying the pitch of the spiral during the first, second and third machining operations so that the pitch increases with increased distance from the tip of the canal instrument.

11. The method of claim 10 which further includes the step of rotating the blank during the grinding.

12. The method of claim 10 wherein the grinding is performed with a grinding wheel, wherein the blank defines a longitudinal axis, and which further includes the step of inclining the grinding wheel relative to the longitudinal axis of the blank.

13. The method of claim 10 wherein the grinding is performed with a grinding wheel, wherein the blank defines a longitudinal axis, and which further includes the step of withdrawing the grinding wheel relative to the longitudinal axis of the blank.

* * * * *